United States Patent [19]

Kirchanski et al.

[11] Patent Number: 5,053,054

[45] Date of Patent: Oct. 1, 1991

[54] METHODS AND REAGENTS FOR STAINING INTRACELLULAR COMPONENTS

[75] Inventors: Stefan J. Kirchanski, Mountain View, Calif.; A. R. M. Azad, Northborough; Peter J. Natale, Canton, both of Mass.

[73] Assignee: Ortho Pharmaceutical Corporation, Raritan, N.J.

[21] Appl. No.: 407,723

[22] Filed: Sep. 14, 1989

Related U.S. Application Data

[63] Continuation of Ser. No. 244,554, Sep. 12, 1988, abandoned, which is a continuation of Ser. No. 92,017, Sep. 2, 1987, abandoned, which is a continuation-in-part of Ser. No. 581,842, Feb. 21, 1984, abandoned.

[51] Int. Cl.[5] .............................................. C09D 69/10
[52] U.S. Cl. ............................................ 8/647; 8/554; 8/648; 8/517
[58] Field of Search .................... 8/517, 554, 648, 647

[56] References Cited

U.S. PATENT DOCUMENTS

| 3,641,235 | 2/1972 | Weiss | 424/8 |
|---|---|---|---|
| 3,652,492 | 3/1972 | Kamogawa et al. | 260/41 |
| 3,761,357 | 9/1973 | Epton et al. | 195/62 |
| 3,764,477 | 10/1973 | Lehmann et al. | 195/63 |
| 3,853,987 | 12/1974 | Dreyer | 424/1 |
| 3,857,931 | 12/1974 | Hager | 424/12 |
| 3,970,597 | 7/1976 | Sokolovsky et al. | 260/72 |
| 3,996,345 | 12/1976 | Ullman et al. | 424/12 |
| 4,035,316 | 7/1977 | Yen et al. | 260/2.5 |
| 4,094,745 | 6/1978 | Scholefield | 435/7 |
| 4,108,972 | 8/1978 | Dreyer | 424/1 |
| 4,166,105 | 8/1979 | Hirschfeld | 424/8 |
| 4,169,137 | 9/1979 | Hirschfeld et al. | 424/8 |
| 4,174,384 | 11/1979 | Ullman et al. | 424/8 |
| 4,199,559 | 4/1980 | Ullman et al. | 424/8 |
| 4,220,722 | 9/1980 | Rowley et al. | 435/188 |
| 4,225,784 | 9/1980 | Barrett | 250/303 |
| 4,228,237 | 10/1980 | Hevey et al. | 435/7 |
| 4,231,999 | 11/1980 | Carlsson et al. | 424/1 |
| 4,267,234 | 5/1981 | Rembaum | 428/403 |
| 4,434,150 | 2/1984 | Azad et al. | 424/1.1 |

FOREIGN PATENT DOCUMENTS 1107644 8/1981 Canada .
0002963 12/1978 European Pat. Off. .

OTHER PUBLICATIONS

Pierce, 1989 Handbook and General Catalog, pp. 209–312.

Primary Examiner—Paul Lieberman
Assistant Examiner—Bradley A. Swope
Attorney, Agent, or Firm—Gale F. Matthews

[57] ABSTRACT

Reagents and methods for intracellular staining of anionic materials as provided. The inherent staining characteristics of a fluorescent molecule may be suitably altered by covalently linking a plurality of said molecules to a nonimmunoglobulin derived cationic polymer having the desired staining specificity. By careful selection of the net charge and size of the dye polymer complex, diffusion through the cellular membrane can be enhanced and an enhanced fluorescent signal obtained by localization of a plurality of fluorescent molecules at the site of interest.

7 Claims, No Drawings

METHODS AND REAGENTS FOR STAINING INTRACELLULAR COMPONENTS

FIELD OF THE INVENTION

This invention relates generally to methods for histochemical staining, and specifically provides reagents and methods useful for staining specific intracellular components without reliance on immunoglobulin derived specificity.

BACKGROUND OF THE INVENTION

It is useful in a number of histochemical applications to be able to differentiate cell types based on their intracellular staining characteristics. Differential staining may reflect the presence or absence of particular organelles, or a difference in degree to which such organelles are present. For instance, the presence of nucleic acid or the amount thereof often serves as useful criteria for determining or distinguishing between various blood cell populations. Further, the ability to specifically stain various intracellular components may provide valuable pathological information concerning various disease states.

It is an object of the present invention to provide reagents and methods capable of exhibiting histochemical differentiation staining characteristics.

Several distinct classes of reagents have been employed to obtain useful intracellular staining. One such class relies solely upon the natural staining properties of dye materials as a means for providing specificity. A dye's natural staining properties refers to the specificity of molecule or cell stained by the dye. For example, the dye acridine orange has a natural specificity for staining DNA. Typically, these dyes are fluorophores which exhibit an emission spectra at a wavelength that is different than the wavelength used to excite the molecule. One example of such a dye is acridine orange and in U.S. Pat. No. 3,798,131, Rounds et al. describe a method for assaying polymeric DNA based on the nucleic acid staining properties of acridine orange.

Fluorophores, however, suffer from the disadvantage that any chemical modifications or manipulations to the fluorescent molecules intended to alter their inherent staining characteristics (i.e so that the dye can stain different classes or a wider range of molecules) also often result in substantial inactivation of the molecule's fluorescent properties. This inactivation apparently results from alteration of the critical three-dimensional structure of the fluorescent molecule which probably alters the molecule's energy transition levels. Consequently, fluorescent molecules often cannot be employed to their full advantage since the specificity of their natural staining characteristics cannot be directly altered without also severely reducing or destroying the molecule's fluorescent staining effectiveness. This is especially true with the so-called red dyes which typically fluoresce more weakly than the acridine orange or fluorescein dye families. Furthermore, chemical modification of the fluorophore intended to enhance direct binding to a target molecule is also problematic because of the same negative effect on the fluorophore's optical properties Despite characteristically weaker fluorescence, red dyes are still preferred in many histochemical applications because a less expensive helium-neon laser may be employed to excite the molecules to fluorescence as compared to the argon lasers necessary to excite fluorescein. Such commercial considerations become especially important with regard to instruments destined for use in the hospital and clinical laboratories where health care operating expenses are already at a premium. Unfortunately, the desirable red dyes not only suffer from weak fluorescence but, like all fluorescent molecules, any significant chemical manipulations designed to increase or improve their staining capability generally also results in serious deleterious effects on their fluorescent properties.

It is an object of the present invention to provide reagents and methods which allow for adjustment or manipulation of staining characteristics without incurring such deleterious associated loss of fluorescence.

One class of methods has attempted to capitalize on the immunological specifity associated with immunoglobulins as a means for altering the inherent staining characteristics of dyes. These methods rely on the immunoglobulin binding to a specific target molecule (thereby providing the desired specificity), wherein the fluorophore is bound to the immunoglobulin. Thus, direct binding of the fluorophore to the target molecule is avoided. One such method is described by Hirschfeld in U.S. Pat. No. 4,166,105 wherein a reagent is provided for the detection of a specific reactant. Such a reactant, generally an antigen, reacts immunologically only with the immunoglobulin which is the specific, complementary homolog for the antigen. By covalently linking a plurality of dye molecules to the immunoglobulin through a polymer such a polyethylene amine, the dye molecules stain materials based primarily on the specificity provided by the immunoglobulin. Thus, the dye molecules become associated only with those materials which express the antigenic determinants for which the antibody is specific.

Although such a reagent can often provide the desired staining specificity for staining, as well as localize a plurality of dye molecules at the desired site, such reagents are often difficult if not impossible to employ satisfactorily on an intracellular basis. This disadvantage is incurred due to the relatively large size of the resultant reagent; the antibody itself typically has a molecular weight of 150,000 daltons, further increased by the weight of the polyethylene amine (typically on the order of 20,000 daltons) plus the weight of a plurality of dye molecules which although comparatively far smaller on an individual basis (in the range of 50-2000 depending on the dye), becomes significant due to the 65 to 80 molecules expected per molecule of polyethylene amine. Such relatively large molecules encounter significant difficulty crossing cellular membranes. Accordingly, their effectiveness as an intracellular staining agent is significantly limited.

It is an object of the present invention to avoid such membrane penetrating limitations by providing reagents and methods which do not rely upon immunoglobulins for obtaining desired staining specificity.

It is a related object to provide reagents having the desired staining characteristics which are significantly smaller on a molecular weight basis than reagents employing immunoglobulin desired specificity.

It is another object to provide methods and reagents which can also localize a plurality of dye molecules at the site of interest whereby fluorescent signal amplification is effected.

Another approach employing immunoglobulin derived specificity has been described in U.S. Pat. No.

4,434,150 (Azad et al.). Therein, a plurality of dye molecules are linked to an immunoglobulin having the desired specificity by means of a polymer having specified charge and size characteristics. Because of the attachment of the relatively large immunoglobulin, however, such a reagent is similarly not preferred for many intracellular applications.

Still another approach attempting to improve intracellular staining is described by Scholefield in U.S. Pat. No. 4,094,745, wherein the microorganisms to be stained are treated chemically to modify the dye receptor sites in the microorganism. The thusly treated microorganisms are thereafter stained with a fluorochrome dye. Such methods, however, disadvantageously alter the natural properties of microorganisms and/or cells and fail to augment staining specificity associated with the dye. They also fail to provide signal enhancement by localization of a plurality of dye molecules at the desired site.

It is an object of the present invention to provide methods which employ reagents capable of carrying a plurality of dye molecules, such as the preferred red dye molecules, to intracellular sites in accordance with desired specificity characteristics without reliance upon immunoglobulin associated specificity or site altering solutions.

SUMMARY OF THE INVENTION

The principles and objects of the present invention are met by providing staining methods for anionic cells or anionic molecules which rely upon cationic reagents comprising a nonimmunoglobulin derived, water soluble organic polymer or copolymer carrier molecule which is suitably constructed to provide the desired staining specificity. The desired staining specificity is for anionic materials. The specificity may be altered by increasing or decreasing the cationic charge on the dye reagent, thereby making the reagent more or less, respectively, attracted to the anionic target material. Covalently attached to the carrier molecule are a plurality of fluorescent dye molecules selected in accordance with desired excitation and/or emission wavelengths. Such fluorescent dye molecules advantageously will exhibit an emission spectra at a wavelength different than the wavelength of excitation illumination. A preferred form of the reagent will comprise polylysine as the carrier molecule having a molecular weight in the range of about 3,000-20,000 daltons although weights up to approximately 100,000 daltons are also useful.

DETAILED DESCRIPTION OF THE INVENTION AND BEST MODE

The present invention provides the desired staining specificity by generally constructing a complex dye "molecule" having a desired cationic charge structure. The desired cationic charge structure will depend on the anionic charge of the cell or molecule to be stained. If the target cell or molecule is highly anionic, then a weakly cationic dye molecule will be sufficient for staining because the forces of attraction between the molecules will be sufficient to bind them together. However, moderate to highly cationic dye molecules will also work. At the opposite extreme, if the target cell or molecule is weakly anionic, then the dye molecule is preferred to be highly cationic. A moderately charged cationic dye molecule could also be used on a weakly charged anionic target, but a weakly cationic dye molecule would not be preferred for such use because binding between the molecules would be too weak and the molecules either would not bind or they would dissociate.

A highly cationic or anionic molecule is one in which substantially all of the available ionizable groups are in positive or negative form, respectively. Similarly, a weakly cationic or anionic molecule is one in which the positive and negative charge structures of the molecule are nearly equal in number, but there is a larger number of positive or negative charges, respectively, so that the net charge is positive or negative, respectively. The relative charge on a molecule can be determined by observing the rate of migration of the molecule in an electric field. Those molecules being highly cationic will rapidly migrate to the cathode in an electric field. Those molecules being highly anionic will rapidly migrate toward the anode in an electric field.

The isoelectric pH of a molecule is that pH at which the molecule carries no net electric charge and fails to migrate in an electric field. The isoelectric pH is determined by the number and pK' of the ionizing side chains, i.e. R groups, on the molecule. It will be relatively high, i.e. above pH 7.0, if the molecule has a relatively high content of positive charges, such as a polypeptide having a high content of the basic amino acids lysine, arginine or histidine. The isoelectric pH will be relatively low, i.e. below PH 7.0, if the polypeptide contains a preponderance of acidic amino acids, e.g. aspartic and glutamic acids. Thus, a highly cationic dye molecule will have an isolectric pH greater than about 7.0 and a weakly cationic dye molecule will have an isoelectric pH less than about 7.0. If the cationic molecule is a polypeptide, it will contain a preponderance of basic amino acids.

As will be readily apparent to one skilled in the art, the net charge on a molecule will be influenced by the characteristics of the medium in which the molecule resides. At any pH above the isoelectric point of a molecule, the molecule will have a net negative charge. Similarily, at any PH below the isoelectric point, the molecule will have a net positive charge. Thus, the cationic dyes of the present invention should be used in a medium having a pH below the isoelectric point of the dye molecule. Furthermore, inorganic anions such as $Cl^-$ or $HPO_4^{2-}$ may bind to the cations of the cationic dye thereby reducing its net positive charge. It is preferred that the cationic dye medium contain little or no interferring inorganic anions.

Since direct alteration of the dye molecule is not practically possible due to the sensitive steric effects upon fluorescent characteristics, a carrier molecule is instead altered as desired. Interference with the fluorescent molecule's structural configuration is to be avoided because such interference would effect the optical properties of the molecule. The carrier molecule provides the desired specificity (i.e. binding to a specific anionic target molecule) and is preferably a low molecular weight, cationic or amphoteric polymer or copolymer which is water soluble. Such cationic dyes are particularly useful for staining the anionic nucleic acids present in the nucleus or cytoplasm of the cell. Other anionic proteins, carbohydrates or glycoproteins within the cell may also be similarly stained.

In the best mode contemplated, the preferred fluorophores are those which are excited by light in the 400-700 nanometer range and more preferably in the range 610-660 nm, which is the range of optimum emission wavelengths of the helium-neon laser. Suitable fluorophores include the fluorescein, acridine, rhodamine, carbocyanine and dicarbocyanine families of dyes. Suitable polymers for use in the present invention are straight chain organic polymers having carbon atoms as the backbone of the chain and positively charged groups or atoms, such as amino groups or nitrogen atoms, as part of the chain backbone or located on side chains. A preferred class of polymers are polypeptides which have positively charged amino acids (i.e. lysine or arginine or histidine). Polypeptides having uncharged polar amino acids such as serine, threonine, glycine and cysteine, or heteropolymers made from a mixture thereof, may also be useful as long as the molecule has a net positive charge. The exact composition of each possible polymer is determined in accordance with the desired specificity toward a given anionic target material. Thus, the relative mixture of the amino acids and the relative charge depends on the target to be used. A generally useful polymer would be, for example, a heteropolymer containing 25% arginine, 10% cysteine, and 65% glycine. Preferred polymers include polylysine or hexadimethrine bromide (a polymer of N,N,N',N'-tetramethylhexamethylenediamine and trimethylene bromide). Hexadimethrine bromide is a straight chain polymer of carbon atoms having positively charged nitrogen groups within the backbone of the chain. Hexadimethrine bromide is not directly labelable with an activated dye as is polylysine. It is contemplated that the dye could be introduced into the polymer through use of a modified 1,3 dibromopropane during the polymerization process. Thus, the label may be introduced into the polymer during polymerization.

The dye molecules or fluorophores used, whether they be cationic, nonionic or anionic, are then covalently linked directly to the reactive polymer using any of the standard protein modification methods commonly known. The dye molecules are preferred to be non-cationic. Preferably, the dye molecules have reactive groups, such as reactive amino groups, which can be activated to bind the dye directly to a corresponding reactive group on the polymer. One example of how this may be done, is by converting an amino group on the dye molecule into an isothiocyanate group which in turn specifically reacts with free amino groups of the polymer backbone. Methods for forming isothiocyanate groups are well known in the art and details are readily available from, for example, *Fluorescent antibody techniques and their applications*, University of Tokyo Press, 1969, Edited by A. Kawamura. Other methods which may be employed to form the covalent linkages include utilizing a number of other reactive groups to link dyes covalently to carboxyl, hydroxyl or sulfhydryl groups on the polymer, and that details of such reactive groups may be found in, for example, *Chemical modification of proteins*, Holden-Day, 1971, by G. E. Means and R.E. Feeney.

The dye molecule may also be linked to the polymer through a linear spacer or linker molecule which has reactive groups at both ends of the molecule. Suitable linker molecules are linear straight chain molecules having from about 4-8 carbon atoms in the backbone of the molecule and having an activatable group at each end of the molecule. Suitable activatable groups are amino, hydroxyl, sulfhydryl or carboxyl groups. An example of a suitable linker is diaminohexadiene. The net charge and molecular weight of the combined polymer-dye should be positive in order to facilitate its diffusion through the outer membrane of the cell or microorganism of interest to the nucleus (if present) or other site of the anionic material to be stained. Biological membranes tend to reject or repel negatively charged molecules, preferring to pass positively charged molecules. It is well know that biological membranes show considerable size discrimination and tend to form barriers to large molecules. Therefore, the preferred polymers are relatively small, such as those found in a molecular weight range of 1,000-20,000. Preferably, the molecular weight of the cationic polymer is in the range of 1,000-5,000. An addition of 10-15 fluorophores on the polymer would increase the molecular weight of the polymer/fluorophore complex by about 1,000-10,000, depending on the molecular weight of the fluorophore. Thus, the molecular weight of the polymer/dye complex may be in the range of about 2,000-30,000 and more preferably within the range of about 2,000-15,000.

Those skilled in the art will readily determine that in some instances, pre-treatment, e.g. permealization, of the cell will tend to enhance the polymer penetration through the membrane and that as the stringency of the pre-treatment or pre-fixation of the cell is increased, one may expect the larger polymers to more readily cross the membrane. Since there are a plurality of dye molecules attached to each reactive polymer, preferably on the order of 10 to 15 dye molecules per polymer, an enhanced fluorescent signal is obtained since a greater number of dye molecules are associated with each interacting site than would otherwise be possible if the dye molecules were employed in the absence of the polymer carrier molecule.

As will now be readily apparent, the ratio of dye molecules to polymer molecules should be carefully controlled during the modification process since an excess of dye molecules attached to the polymer will tend to result in an undesirable masking of the polymer's binding characteristics and/or charge characteristics. Accordingly, the number of dye molecules will preferably be limited on the order of about 10-15 per polymer carrier molecule so that the net charge of the reagent will be positive.

The number of dye molecules that attach to the polymer backbone may be limited by any of the methods well known in the art for limiting the extent of a chemical reaction. In one case, the number of amino groups, which is the number of possible attachment sites, may be limited in the polymer backbone. Also, the time of reaction can be limited so that only a few dye molecules have a chance to bind to the polymer. Also, the amount or number of dye molecules can be limited by using a molar excess of polymer molecules to dye molecules. Finally, a combination of any of the above may be used to limit the number of dye molecules binding to the polymer.

The carrier polymer-dye molecule complex of the present invention may be employed to distinguish cells by intracellularly staining anionic structures within the cells, removing any excess or unreacted molecule complexes and then illuminating the cells under conditions suitable for eliciting a fluorescent response. The fluorescence may be detected by any of a number of well-known techniques such as by fluorimetry and, based on the responsive signal produced by the fluorescence detector, differentiation of cell types may be accomplished.

The intracellular penetration of the carrier-dye molecule complex of the present invention may be advantageously enhanced by several methods. Such methods include treating the cells with solutions such as paraformaldehyde or formalin in order to enlarge membrane pores. Another method involves treating the cells with chelating agents in order to free anionic sites. An additional method involves increasing cellular uptake of the molecule complex by applying an appropriate electric field or pH environment. Although not required because of the relative small size of the carrier-dye complex such penetration enhancement methods may be advantageously selected by the investigator in accordance with the cells to be differentiated.

For instance, the present invention has been advantageously used to differentiate, in blood samples, between lymphocytes which stained relatively well with a polylysine-fluorescein complex formulated in accordance with the principles of the present invention, reticulocyes which stained to an intermediate degree and erythrocytes which stained very poorly.

Such differentiation capability provides not only greater counting facility but also superior accuracy, particularly in the so-called flow cytometric type of blood analyzing instruments. Still other uses suggest themselves and include the identification or location of plasmids or other genetically engineered nucleic acid materials in fluid as well as the identification, localization or differentiation of cells generally in situ.

Based on the foregoing, it will be readily apparent to one skilled in the art that numerous alternatives and modifications of the foregoing will be possible, particularly with respect to the selection and size of the polymers and the selection and number of the fluorescent dye molecules, without departing from either the spirit or the scope of the instant invention.

What is claimed is:

1. Cationic staining reagent comprising polylysine molecule covalently attached to a plurality of fluorescent dye molecules.

2. Cationic staining reagent of claim 1 wherein said polylysine molecule is covalently attached to said dye molecules by converting an amino group on a dye molecule into an isothiocyanate group which in turn specifically reacts with free amino groups of the polylysine backbone.

3. Cationic staining reagent of claim 1 wherein said polylysine molecule is colvalently attached to said dye molecules by activating reactive groups on said polylysine.

4. Cationic staining reagent of claim 3 wherein said reactive groups are selected from the group consisting of carboxyl, hydroxyl and sulfhydryl.

5. Cationic staining reagent comprising polylysine molecule covalently attached to a plurality of fluorescein molecules.

6. The reagent of claim 1, wherein the reagent has from about 10 to about 15 dye molecules covalently attached to each said polylysine molecule.

7. The reagent of claim 1, wherein said fluorescent dye molecules are selected from the group consisting of rhodamine, acridine, fluorescein, carbocyanine, dicarbocyanine, and fluorescent dyes whose characteristic excitation wavelength falls within the wavelength range of 610–660 nm.

* * * * *